US 7,077,075 B2

(12) United States Patent  
Holyoak

(10) Patent No.: US 7,077,075 B2  
(45) Date of Patent: Jul. 18, 2006

(54) ACTIVATED FEED THROUGH, FEEDING SYSTEMS INCORPORATING SAME, AND METHODS OF USE OF SAME

(76) Inventor: H. Kenneth Holyoak, Highway 129 North, Alapaha, GA (US) 31622

( * ) Notice: Subject to any disclaimer, the term of this patent is extended or adjusted under 35 U.S.C. 154(b) by 94 days.

(21) Appl. No.: 10/820,090

(22) Filed: Apr. 7, 2004

(65) Prior Publication Data

US 2004/0194717 A1    Oct. 7, 2004

Related U.S. Application Data

(60) Provisional application No. 60/460,968, filed on Apr. 7, 2003.

(51) Int. Cl.  
*A01K 39/04* (2006.01)  
*A01K 39/01* (2006.01)
(52) U.S. Cl. .................................. 119/456; 119/51.04
(58) Field of Classification Search ............... 119/416, 119/417, 456, 457, 51.04, 57.2, 57.91, 57.92, 119/471  
See application file for complete search history.

(56) References Cited

U.S. PATENT DOCUMENTS

| | | | | |
|---|---|---|---|---|
| 3,095,852 A | * | 7/1963 | Goldman | 119/51.04 |
| 4,027,627 A | * | 6/1977 | Fillion | 119/57.91 |
| 4,038,947 A | | 8/1977 | Lester, Jr. | |
| 4,347,808 A | | 9/1982 | Lester | |
| 4,697,547 A | * | 10/1987 | Malestein | 119/457 |
| 5,150,666 A | * | 9/1992 | Momont et al. | 119/57.91 |
| 5,873,327 A | | 2/1999 | Holyoak | |
| 6,257,170 B1 | * | 7/2001 | Gundersen | 119/456 |
| 6,314,910 B1 | * | 11/2001 | Tracy | 119/51.04 |
| 6,341,577 B1 | | 1/2002 | Holyoak | |
| 6,571,736 B1 | * | 6/2003 | Patterson et al. | 119/51.04 |

* cited by examiner

*Primary Examiner*—Michael J. Carone  
*Assistant Examiner*—Elizabeth Shaw  
(74) *Attorney, Agent, or Firm*—Joseph Fischer; Beusse, Wolter, Sanks, Mora & Maire, P.A.

(57) ABSTRACT

A feed trough is provided for use in cultivation containers for growing frogs and other amphibians. The feed trough is comprised of a sloped floor. In some embodiments the floor slopes downward to an opening from which, during operation, airflows. The opening is covered by a perforated cover that retains the feed particles collected from the sloped floor and provides sufficient opening for airflow that propels the feed particles from the perforated cover into the airspace of the cultivation container.

During operation, airflow passes through the opening with sufficient force to suspend in the air feed particles that have rolled along the sloped floor, or fallen, onto the perforated cover covering the opening. The movement of the feed particles in the air stimulates feeding by the frogs or other amphibians. Feed that is not consumed falls onto the sloped floor, rolls onto the screen or wire mesh covering the opening, and is resuspended by the airflow. The airflow may be continuous, intermittent, or otherwise programmed.

The air of the airflow may be heated. This serves to dry feed particles that have become moistened, increase ambient temperature to increase growth rates, and/or dry the cultivation container.

In other embodiments a vibrational force is applied to move feed particles to simulate live feed, to stimulate feeding.

17 Claims, 8 Drawing Sheets

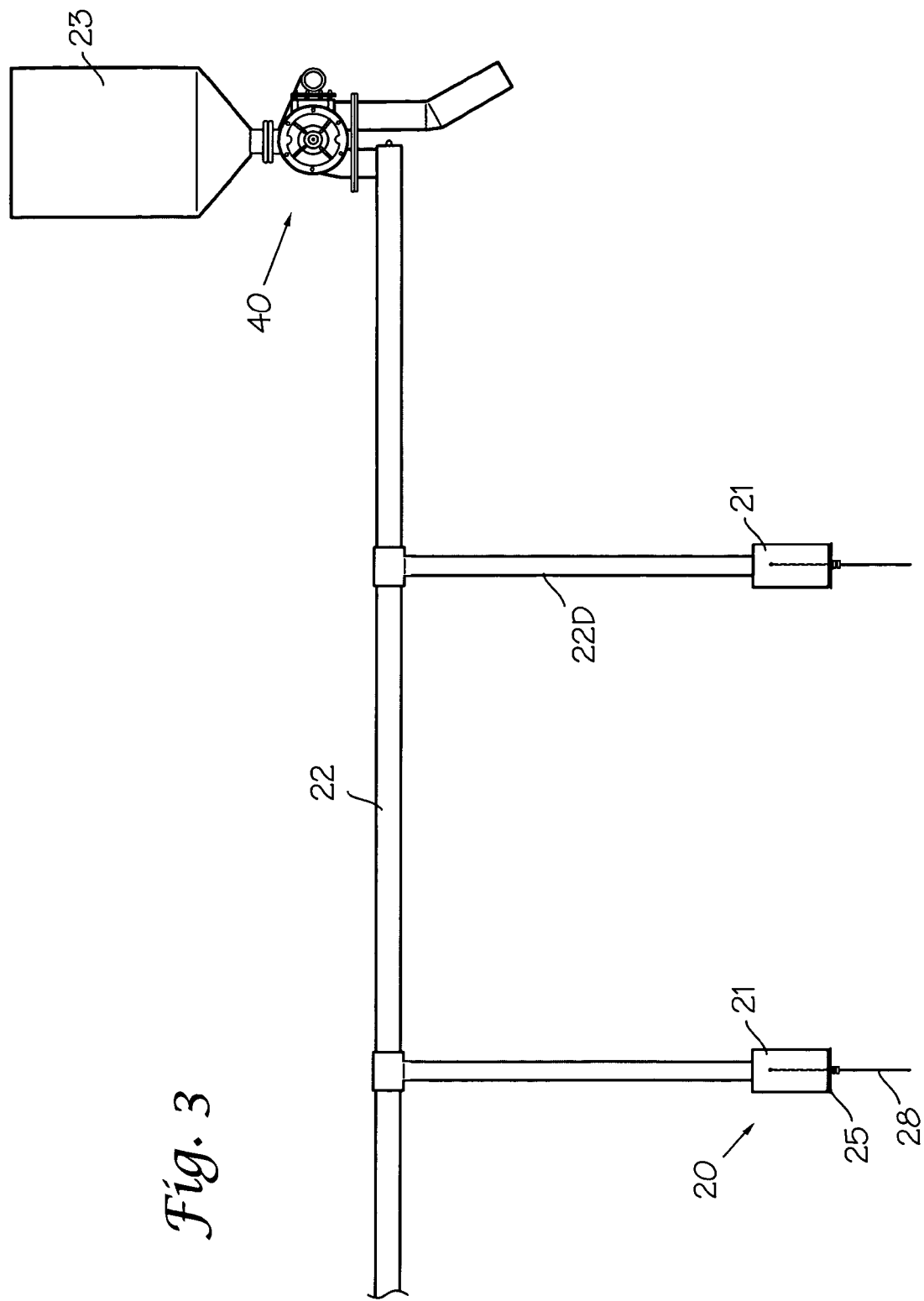

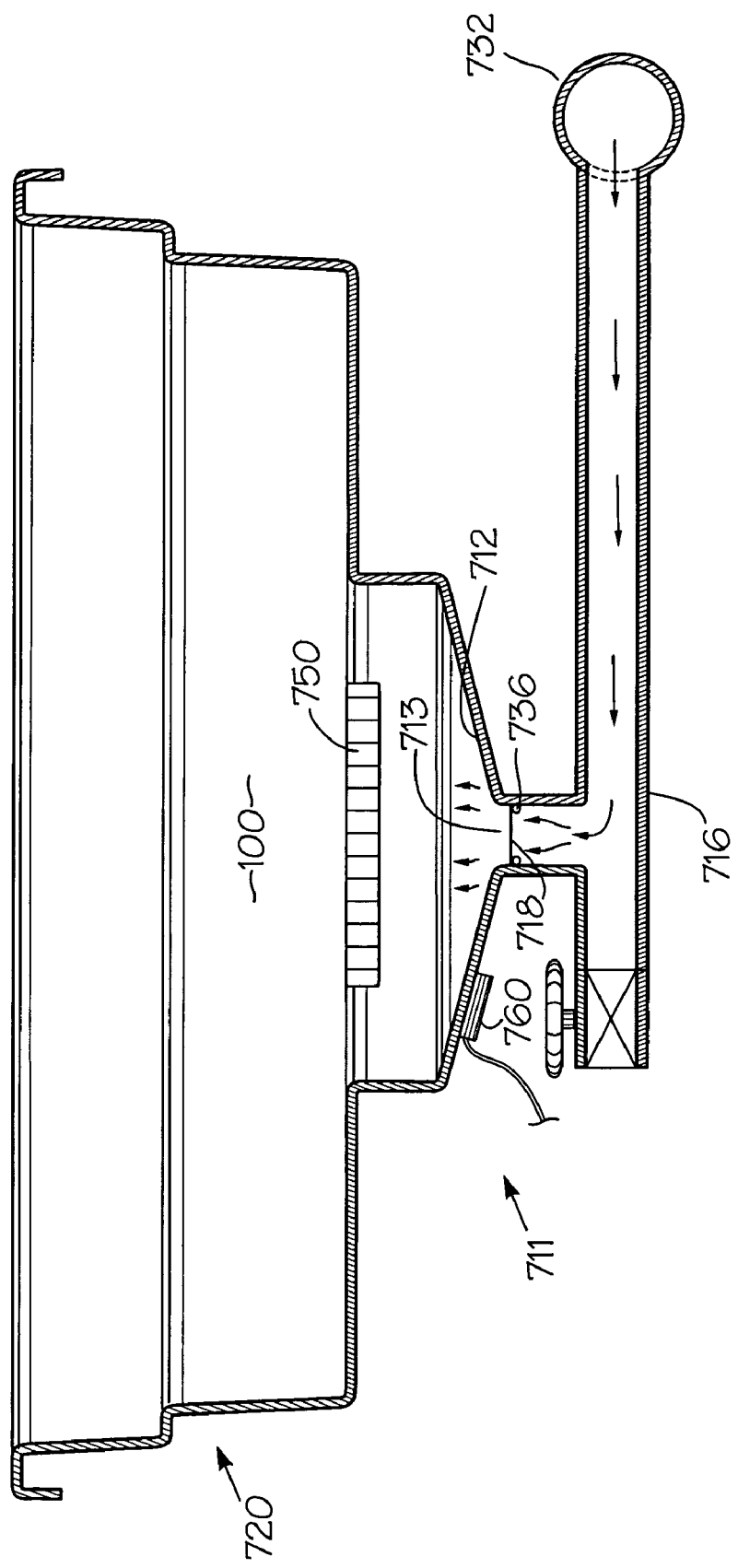

ACTIVATED FEED THROUGH, FEEDING SYSTEMS INCORPORATING SAME, AND METHODS OF USE OF SAME

CROSS REFERENCE TO RELATED APPLICATIONS

Under 35 USC § 119(e), this application claims the benefit of U.S. Provisional Application Ser. No. 60/460,968, filed Apr. 7, 2003.

FIELD OF THE INVENTION

The field of this invention relates to the cultivation of amphibious animals, such as frogs, and specifically to methods, devices and systems used in feeding frogs.

BACKGROUND

The captive cultivation of amphibians, such as frogs, requires devices, methods and systems specialized to particular needs and phenomenon of the animals being raised. In that most amphibians require frequent contact with water, the presence of ample water, often for immersion, in a cultivation system can lead to problems in other aspects of the cultivation system. For instance, cultivation containers maintain a small pool of standing water for frogs. The frogs periodically enter and leave the pool, and upon leaving track water across the floor of the habitat container. These wet frogs may stand on or walk across feed particles, thereby wetting, breaking, and dispersing the feed throughout the container. This results in fouling of the container and lowering of feed conversion efficiency. Thus, the substitution of processed feeds for live feeds can lead to problems such as feed spoilage, non-utilization of feed, and disease, as when most of the feed is not eaten and/or when spoiled feed is not timely removed.

Particularly in the case of frogs, development and utilization of effective feeding systems can promote high growth rates and feeding efficiency while reducing feed loss, feed spoilage, and the chance of disease outbreaks. Various approaches to feeding frogs held in a wall-enclosed container have been attempted. For example, some in the art have blended live fly larvae with dry feed pellets in a feeding area on the bottom of a container housing frogs. The movement of the fly larvae attracts the frogs and stimulates feeding. Both the dry feed pellets and the fly larvae are consumed. While this system can be effective at encouraging frogs to consume dry feed, the need to continuously culture flies to obtain fly larvae for this approach adds to the costs and efforts to raise the frogs. Also, there is added risk of relying on live feed. If a large frog raising operation depends upon fly larvae for effective feed utilization and the fly culture operation experiences a crash, then the frog raising operation suffers substantially.

Other approaches have been advanced to get frogs to eat non-living feeds in captive environments. These efforts are directed in various ways to overcome the frogs' reluctance to eat non-moving, artificial feeds such as pellets or ground feed particles. Among these approaches are those described in the following U.S. Pat. Nos. 4,347,808; 4,038,947; 5,873,327; and 6,341,577. All patents, all patent applications, all patent publications, and all other publications cited herein are incorporated by reference to the same extent as if each individual publication or patent application was specifically and individually set forth in its entirety, and are particularly incorporated by reference for the relevant teachings disclosed herein.

However, for one or another reason the approaches known in the art have not proved consistently effective over long periods the culture for large numbers of containerized frogs. Among the reasons are fouling of moving parts, accumulation of overly moist feed, and the need for ongoing adjustment of mechanical linkages. Thus, there is a need for effective methods, devices and systems for use in feeding frogs and other, similarly behaving amphibians in captive cultivation vessels.

SUMMARY OF THE INVENTION

The present invention is for a system, apparatus, or method which causes feed to move in the cultivation container in which are housed frogs or other amphibians. In an exemplary embodiment of the present invention, an air-activated feeding trough disposed on the bottom of a growing cubicle (i.e., vessel or container) is comprised of inclined floors surrounding a central opening. A perforated cover disposed over the central opening is comprised of a wire mesh or screen sized to retain the feed particles and provide sufficient open space to permit sufficient airflow to propel the feed particles into the airspace of the cultivation container. The slope of the inclined side walls is such that feed particles roll down and onto the perforated cover. Airflow from an air source blows upward through the opening with sufficient force to drive the feed particles upward from the perforated cover, to make them airborne for a period. Feed particles moving through the air stimulates feeding by the frogs. Airborne feed particles that are not eaten fall to the sloped side walls, roll down and are repeatedly made airborne by the forced air current. This cycle repeats so long as the forced air current is operative and feed particles remain. In various embodiments the air is set to operate at specific intervals or cycles, or in some embodiments may operate continuously, depending on the specific interests, factors and constraints of a particular cultivation operation.

In certain embodiments of the present invention, a demand feeder is positioned in the growing cubicle so that feed distributed from it falls to a feeding trough such as described above. A demand feeder generally comprises a container from which a portion of feed falls upon activation by the frogs or other amphibians in the growing cubicle. For example, not to be limiting, a movable rod extends down from a demand feeder toward the floor of the growing cubicle. A top end of the rod is pivotally attached to the feeder and the rod also is attached to a plate restricting feed at the bottom of the feeder. As frogs move, they bump the rod, actuating the rod from vertical. The rod pivots tilting the plate so that feed egresses through a gap between the plate and the feeder body and drops from the plate to the frogs below. Feed particles that are not immediately consumed enter the feeding trough, where they are periodically made airborne as described above. This increases feed utilization.

In certain embodiments of the system of the present invention, a feed distribution network supplies a number of demand feeders that supply a number of growing cubicles, and each demand feeder is positioned above a feeding trough so feed released by the demand feeder falls onto the feeding trough. This achieves feeding on demand and iterative stimulation for feeding as the forced air current resuspends feed into the air.

In other embodiments of the present invention, the temperature of the forced air current is elevated, as by application of a heater to the air supply. This achieves one or more of the following: drying feed particles that have become moistened; raising the ambient temperature to a range more conducive for growth; and drying the cultivation container so as to lessen the incidence of molding feed and/or disease outbreaks.

In other embodiments of the present invention, a vibrational force is applied to move feed particles to simulate live feed to stimulate feeding behavior.

Other aspects, advantages and objects of the present invention are provided in the following description, which is to be considered with the appended drawings.

BRIEF DESCRIPTION OF THE DRAWINGS

The features of the invention believed to be novel are specifically set forth in the appended claims. However, the invention itself, both as to its structure and method of operation, may best be understood by referring to the following description and accompanying drawings.

FIG. 3 provides a diagram of a part of one embodiment of a feed delivery system used in the present invention.

FIG. 7 is a cross-sectional view of another embodiment of a cultivation container of the present invention comprising a built-in feed trough.

DESCRIPTION OF THE INVENTION

Throughout the description of the invention, particularly the embodiments disclosed herein, it is appreciated that like numbers of components represent similar or identical structures. Also, as used throughout this disclosure, including the claims, "growing cubicle" and "cultivation container" are taken to mean a container having a bottom wall with a continuous upstanding side wall extending about the periphery of said bottom wall, of a size suitable for the cultivation in captivity of frogs and other amphibians. One or more of the side wall sections may be comprised of a mesh or screen, so long as the functionality of keeping captive the frogs or other amphibians is maintained. The two-dimensional shape of a cubicle is not limited to a square shape; cubicles may be rectangular, circular, and other shapes as desired. Other terms that are interchangeable with "growing cubicle" and "cultivation container," when used in the proper context, are "container" and "vessel." Also, while the main use of growing cubicle incorporating the present invention is for the growth of frogs and other amphibians of interest, the present invention may be used and be part of growing cubicles that are used for maintenance of brood stock and other purposes not immediately directed to a "grow-out" type operation (i.e., not focusing on growth as measured by weight gain over time).

As used throughout this disclosure, including the claims, the terms "feed trough," "feeding trough," and "trough" are taken to mean a component or subcomponent (of a cultivation container) having described features that provides for the collection, retaining, and periodic or continuous distribution of feed particles into the airspace of the cultivation container. The use of the word 'trough' is not meant to limit "feed trough," "feeding trough," and "trough" to one of the common meanings pertaining to a structure that is long and narrow. Rather, a "feed trough," "feeding trough," and "trough" of the present invention may be formed to be round, rectangular in any proportions of length and width, or any other suitable shape. Also, as used throughout this disclosure, including the claims, the term "feed collection area" is taken to mean an area of a cultivation container across which feed particles are made to move to simulate live feed, to stimulate feeding. A feed collection area may comprise a "feed trough" as that term is defined herein, or may utilize other means for moving as described herein.

As used herein, the terms "feed," "artificial feed," and "feed particle" refer to pellets, granules, ground or ground and sized particles, extruded shapes, and any other form of non-living nutritional composition provided to the cultivation containers to support the growth and maintenance of the frogs or other amphibians housed therein.

Figure 1:
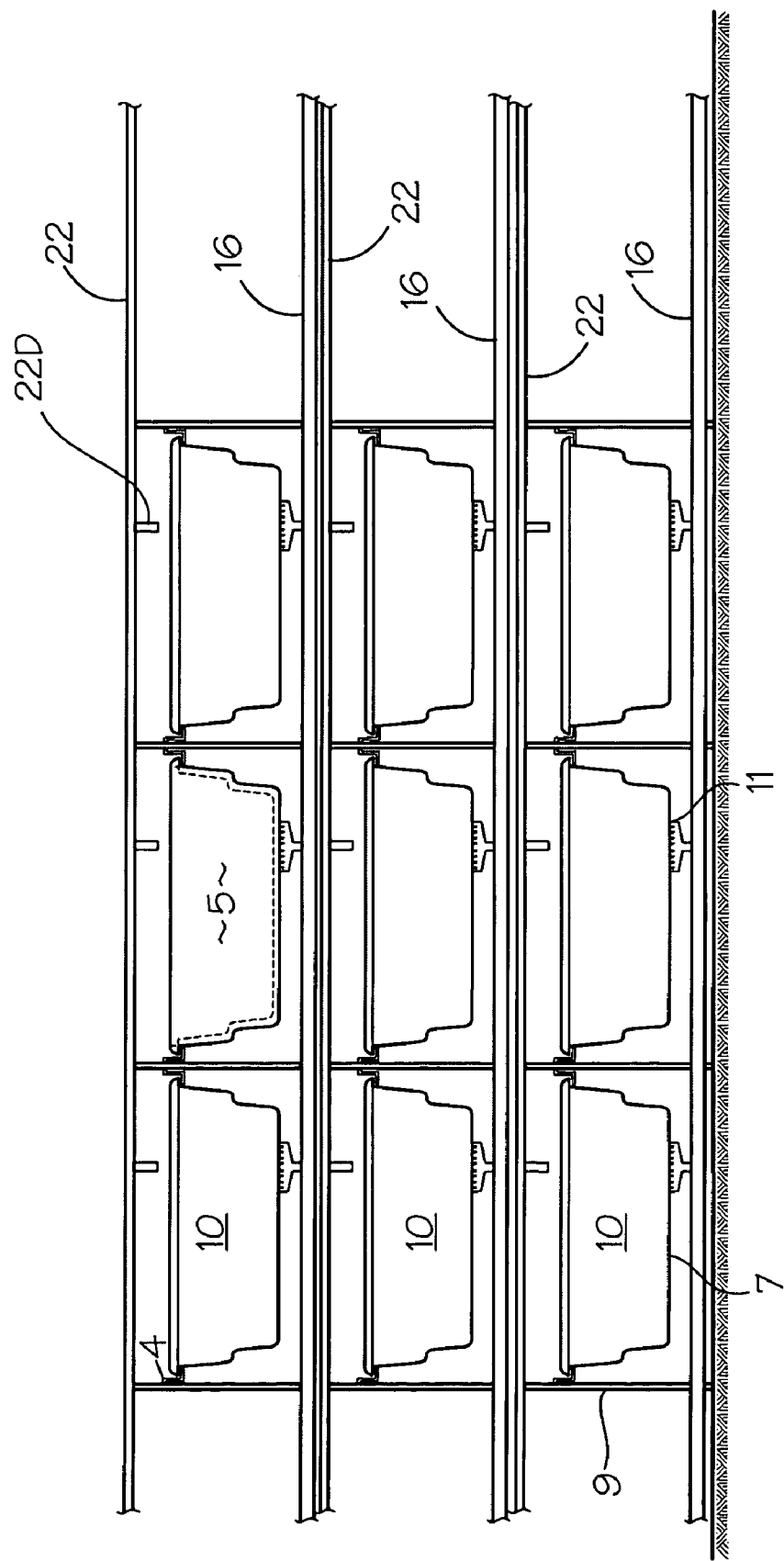
FIG. 1 is a side view of an array of growing cubicles for the cultivation of frogs, positioned on racks, and supplied with feed and air.

The present invention may be incorporated into a single growing cubicle or an array 1 of growing cubicles 10, as shown in FIG. 1. An array 1 of growing cubicles 10 is mounted on a rack system 9 via braces 4, supported on a floor, and a feed trough 11 is mounted to or integral with the underside of each growing cubicle 10. As depicted in FIG. 1, each growing cubicle 10 is comprised of a cubicle floor 7 for supporting the animals, and cubicle sidewalls 6 connected to the floor 7 extending upward there from and forming an interior 5 of the cubicle 10. It is noted that although the floor 7 is shown to be horizontal in FIG. 1, in various embodiments the floor is sloped along its entire span or only in certain sections, or is subdivided to a horizontal area and a sloped area. For instance, not to be limiting, a floor of a container may be subdivided to comprise a first area in which a water pool is provided, and a second area where feeding takes place.

Figure 2A:
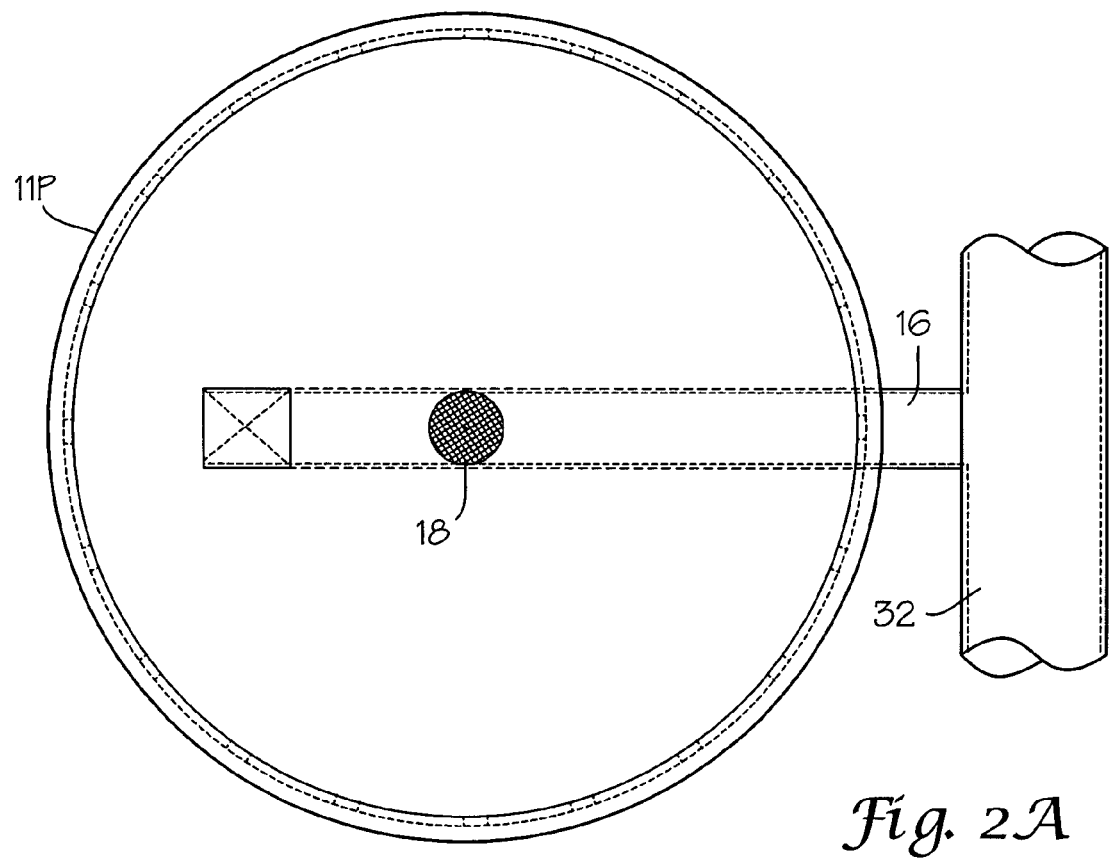
FIGS. 2A and 2B provide, respectively, a top and a cross-sectional view, through the middle, of one embodiment of a circular air-activated feed trough.
Figure 2B:
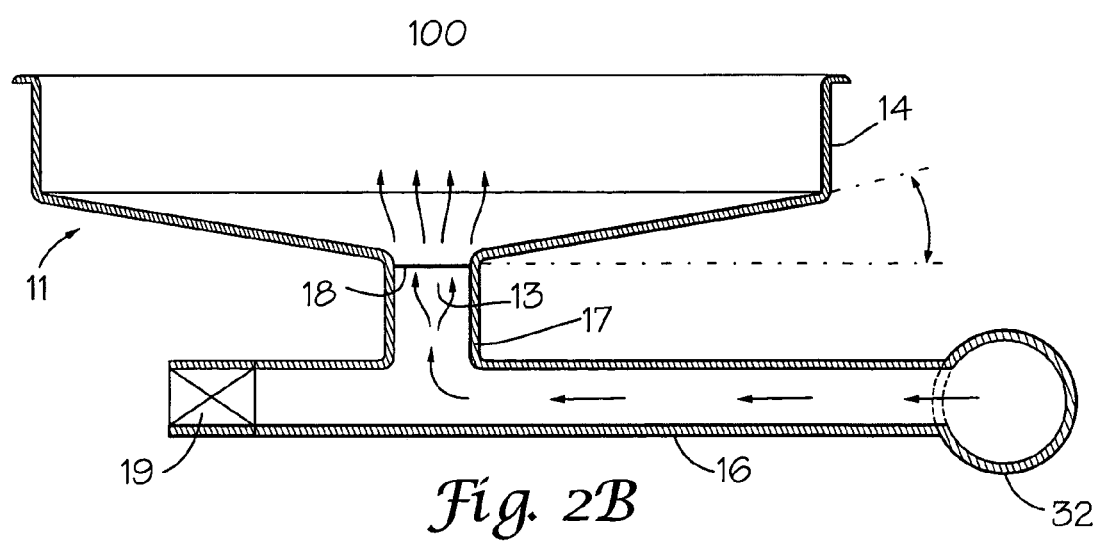

A single feed trough 11 is shown in more detail in FIGS. 2A and 2B which provide, respectively, a top and a cross-sectional view, through the middle, of one embodiment of a circular air-activated feed trough. The feed trough 11 is comprised of a circular perimeter 11P defining the top edge of a vertically disposed trough wall 14. The bottom edge of the trough wall 14 connects to trough floor 12, which inclines downward at an approximately 10–15° angle below horizontal to an opening 13. In certain embodiments (not shown) in which a trough wall (such as 14) is not included, the outside perimeter (whether circular, rectangular, etc.) defines the outer edges of the sloped floor.

Air is supplied to the trough 11 by air inlet tubes or air lines 16 via a connector pipe 17, which terminates at the opening 13. At the other end of the air system the air lines 16 are connected to an air compressor and/or blower (not shown) via one or more trunk lines 32. The air compressor and/or blower provides air for supply and distribution to the feed trough 11 (and to other feed troughs in the system). A perforated cover 18 is secured over the opening 13 to prevent feed from falling into and clogging air tube 16, and to make available collected feed particles for propelling into the air space of the cultivation container by airflow as described herein.

In certain embodiments, drain holes (not shown) may be made in the trough floor 12. During cleaning operations or other operations where excess water is in the growing cubicle 10, water flows out from these drain holes. When growing cubicles 10 are in a stacked array, as shown in FIG. 1, such water exiting through these drain holes may fall onto a drain system (i.e., a trough or open pipe, not shown) and be so carried away, may fall into the growing cubicle 10 directly beneath it (and then onto the floor or a drain system below the bottom growing cubicle 10), or may be otherwise directed for disposal. Also, it is noted that trough wall 14, while depicted in this and other embodiments herein, is an optional feature.

Rather than fixed and rigid (i.e., PVC pipe) air connections to the cultivation containers, such as depicted in FIGS. 1 and 2A and 2B, a variety of arrangements of removable flexible tubing may be used. For example, not to be limiting, an air blower for a facility comprising a number of cultivation containers (such as arranged in FIG. 1) has a 15 inch rigid PVC trunk line leading to a plurality of 4 inch rigid PVC intermediate supply lines. From such intermediate supply lines a plurality of flexible plastic 1.5 inch or 2.0 inch hoses are connected. Each such hose then goes to a cultivation container, to supply air to the opening of the feed trough, so that upon supplying sufficient airflow, the airflow propels feed particles that fall into the opening.

In certain of such embodiments, the flexible hoses to each cultivation container's feed trough are readily removable by hand, so that daily or periodic cleaning of the cultivation container can be achieved by disconnecting the air supply hose, moving it to one side, and then washing out the cultivation container, with the water flowing out the opening onto the ground, into a cultivation container below, or into a drain. Then, after the cleaning, the connection is reestablished. For example, not to be limiting, a flexible hose may travel horizontally from the intermediate supply line to beneath a cultivation container, then bend or elbow upward, and connect to the feed trough. A set screw or other fastening means may be used to reversibly hold the flexible hose in place on the feed trough, such as to a fixed pipe attached to the bottom of the feed trough. Any connecting methods and piping and hose configurations as are known to those skilled in the art may be used to provide a fixed (i.e., glued) or removable communication of air to the cultivation containers from an air supply source.

As a further example, not to be limiting, the entry of the air may be provided in a "tee" beneath the feed collection area of the cultivation container. That is, two ends, a top and a bottom end, of a rigid tee are aligned vertically beneath the entrance of air to the feed collection area (i.e., directly in line and below the connector pipe 17, which terminates at the opening 13, of FIGS. 2A and 2B). The top end connects to form a fluid communication with the opening for airflow into the feed collection area. The bottom end is fitted with a valve that may be reversibly opened and closed, and adjusted to be partially open. The third end of the tee is disposed horizontally, and connects to the air supply (i.e., connects to air line 16 of FIGS. 2A and 2B). With such arrangement, during periodic cleaning with water of the cultivation container, the valve is opened and this allows the water to freely flow out, taking with it excess feed, feces, etc., from the cultivation container. After this cleaning operation is completed, the valve is closed completely or partially. The valve may be adjusted (thereby only closed partially) in order to control the air flow into respective cultivation containers, to obtain a desired level of propelling of feed particles into each of the cultivation containers.

As shown in FIG. 1, feed dispensing tubes 22 extend across a respective rack level and drop feed down via 22D into each growing cubicle 10. In certain embodiments the growing cubicle 10 has a generally sloping cubicle floor 7, so that feed will tend to roll or otherwise travel down to the trough 11. In some of such embodiments (not depicted in FIG. 1) the feed tubes 22 dispense feed above the growing cubicle 10 so that the feed will fall within the growing cubicle 10 onto the cubicle floor 7 and travel down and across a portion of the cubicle floor 7 to the trough 11. In other embodiments, such as is depicted in FIG. 1, each feed tube 22 is disposed above the feed trough 11 in the respective growing cubicle 10. In these latter embodiments the feed falls onto the area defined by the feed trough 11. Air supplied to the trough 11 through opening 13 causes the feed pellets (not shown) to move within the trough 11, simulating live feed for the frogs.

The air lines 16 are connected to an air compressor or blower (not shown) of sufficient volume to generate airflow at a rate, or pressure, capable of moving the feed to simulate live food. Each air line 16 may have a valve 19 mounted adjacent the end of the air line 16 for flushing feed particles or other matter from the air line 16. Where a line of growing cubicles 10 are supplied by a straight section of air line 16, a single valve 19 may be disposed at the end of the air line 16, opposite a supply trunk (not shown in FIG. 1) that supplies the air.

Generally, a growing cubicle and a feed trough may be molded as one single unit, or the feed trough may be mounted to the bottom of the growing cubicle as a separate component. The feed trough may be any desired shape and may occupy a range of percentages of the bottom surface area of a cultivation container (of which the growing cubicle 10 in FIG. 1 is one example). For example, not to be limiting, the feed trough 11 may be rectangular or circular in shape, and the feed trough 11 may occupy anywhere from about 10 percent to about 100 percent of the bottom surface area of the cultivation container.

One example, not to be limiting, of approximate dimensions of a cultivation container and feed trough are as follows: 30 inches across top of cultivation container; nine inches distance between top and floor of cultivation container; 2 inches height of feed trough vertical wall; and an integral feed trough disposed from the cultivation container floor, having a diameter between about six and about 12 inches, and having a trough floor with a 10–15 degree inclination downward to a central opening for airflow.

A range of possible cycles and feeding regimes may be used with the present invention. For instance, not to be limiting, a single blower may be used continuously to blow air into a number of cultivation containers to elevate the feed particles into the air. Alternatively, without being limiting, a blower may only be used during daylight hours, at specific intervals (i.e., every hour for 15 minutes), or at specified times each day (i.e., at 0900, 1300 and 1800, for 30 minutes). Also, the air may be blown in at times related to adding feed to the feed tubes.

The force of the air blown into the cultivation containers is designed to propel feed particles into the air about three to four inches, more generally about two to four inches, and even more generally about two to six inches into airspace 100 from the level of the perforated cover to which the feed particles periodically return. Airspace 100 is the inside otherwise unoccupied interior 5 of cultivation container 10, and may include the space defined by the feed trough 11 of the cultivation chamber 10. Accordingly, the volume and pressure of the air blown into the cultivation containers is adjusted as needed to result in feed being elevated upward from the perforated cover within these ranges. This may be adjusted from a central control or valve for a plurality of cultivation containers, or valves or other control devices may be provided for each cultivation container. Further, it is appreciated that although it is within the scope of the present invention that the air may propel some or all feed particles even higher than six inches, in doing so the risks increase that some feed particles will be propelled outside the growing cubicle or into a water pool also in the growing cubicle, thereby fouling the water in the pool.

Without being bound to a particular theory, the several movements of the feed resulting from practice of the methods of the present invention in the devices and systems of the present invention individually or cumulatively stimulate feeding. For instance, not to be limiting, when airflow propels feed from perforated cover 18 into the airspace 100, individuals of the cultured species, such as frogs, are stimulated to capture and eat the feed while it is being propelled through the airspace 100. Most or all feed particles that are not consumed during their respective airborne trajectories fall to the sloped floor 12, and begin to roll toward the perforated cover 18. This movement also stimulates some individuals, who will feed on the particles while they roll, or once the stop. As a result of the feeding behavior being so stimulated, some individuals also may feed on feed particles that have come to rest, either along the sloped floor 12 or on the perforated cover 18. Thus, through one or more of these, feeding behavior is stimulated.

It is noted that in FIG. 1 the connector pipe 17 that directs air upward through the perforated cover 18 and into the growing cubicle 10 is disposed in an axis at a 90 degrees angle to horizontal. This tends to direct the air directly upward. However, this configuration is not meant to be limiting. That is, in some embodiments the connector pipe is disposed at an angle other than 90 degrees to horizontal. An illustrative example of an alternative, not to be limiting, is that a connector pipe is oriented and directs air at 75 degrees to horizontal, and the shape of the feed trough floor 12 conforms to the expected travel and landing area of the feed particles so elevated by the angled airflow. This directs the feed into a more concentrated pattern, as may be desired in certain arrangements of a cultivation container. Also, consistent with the latter, it is appreciated that in certain embodiments only one sloped floor exists, such as to one side of an opening angling airflow and feed particles to fall only on that sloped floor. It is further appreciated that any form of constriction in the air tube construction before the opening may be employed to change the air velocity to a more desired velocity for the circumstances.

Figure 4:
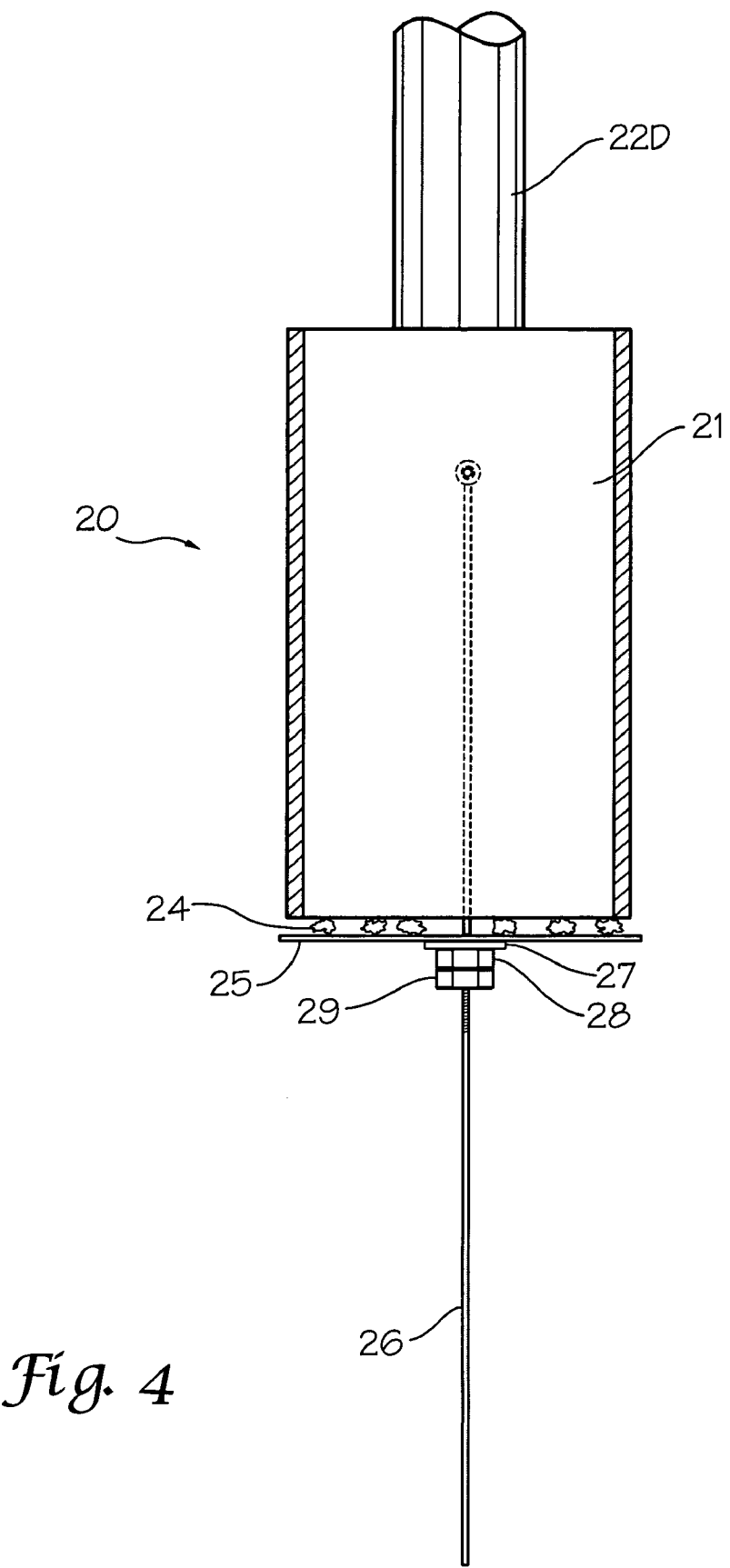
FIG. 4 is a side view of one embodiment of an automatic feed dispenser of the present invention.

In some embodiments, a feed dispenser 20, shown in FIGS. 3 and 4, is used to automatically dispense feed when frogs are feeding, and, more generally, when frogs activate the feeder by a movement. The dispenser 20 includes a cylinder 21 connected to a feed discharge tube 22, which is linked to a feed hopper 23. A rotary valve 40, such as a twin-outlet rotary valve manufactured by Bush & Wilton, Inc., distributes feed from hopper 23 to feed discharge tube 22. Feed pellets 24 are discharged from the hopper 23 via the tube 22 to substantially fill the cylinder 21. In the embodiment depicted in FIG. 3, a drop tube 22D component of the discharge tube 22 is connected to a top end of the cylinder 21 to supply feed, and a plate 25 is disposed at a bottom end of the cylinder 21 to control the distribution of pellets 24 from the cylinder 21. As depicted in FIG. 4, the plate 25 is spaced below the otherwise open bottom end of the cylinder 21 so pellets 24 may fall from the cylinder 21.

More particularly, the position of the plate 25, with respect to the cylinder 21, controls the amount of feed, or number of pellets 24, discharged from the cylinder 21. The position of the plate 25 is adjusted along a longitudinal axis of rod 26, which is pivotally attached along a rod 30 that passes through the walls of cylinder 21. In a preferred embodiment, an assembly comprising a washer 27, a first nut 28 and a second nut 29 are used to adjust the position of the plate 25 along the longitudinal axis of the rod 26. Once a desired distance is established between the plate 25 and the bottom of the cylinder 21, the second nut 29 is tightened against the first nut 28. The rod 26 extends downward within the growing cubicle 10. When frogs are feeding, the frogs will bump the rod 26, causing it to pivot, moving plate 25 and causing pellets 24 to fall from the cylinder 21 into the growing cubicle 10 and trough 11. Alternatively, while moving in the area of the rod 26, frogs may incidentally bump the rod 26, causing it to pivot and release feed, thereby adding feed that is available for feeding at that time or at a later time. This may induce feeding activity for a period. The position and the height of the rod 26 above the floor 7 or trough floor 12 are adjusted so that movement by the frogs against the rod 26 provides a satisfactory feed input.

It is noted that small frogs may not be able to bump the rod 26 of the feeder sufficiently to obtain a desired amount of feed particles from the feed dispenser 20. Accordingly, in certain embodiments a vibrator (not shown) is attached to the rod 26 or the plate 25, and the vibrator is operatively connected to a timer (not shown). The timer periodically activates the vibrator, which vibrates sufficiently to release feed particles from between the bottom edge of the cylinder 21 and the edges of the plate 25. These embodiments may be used for small frogs as well as under other circumstances and with other amphibious species.

Figure 5:
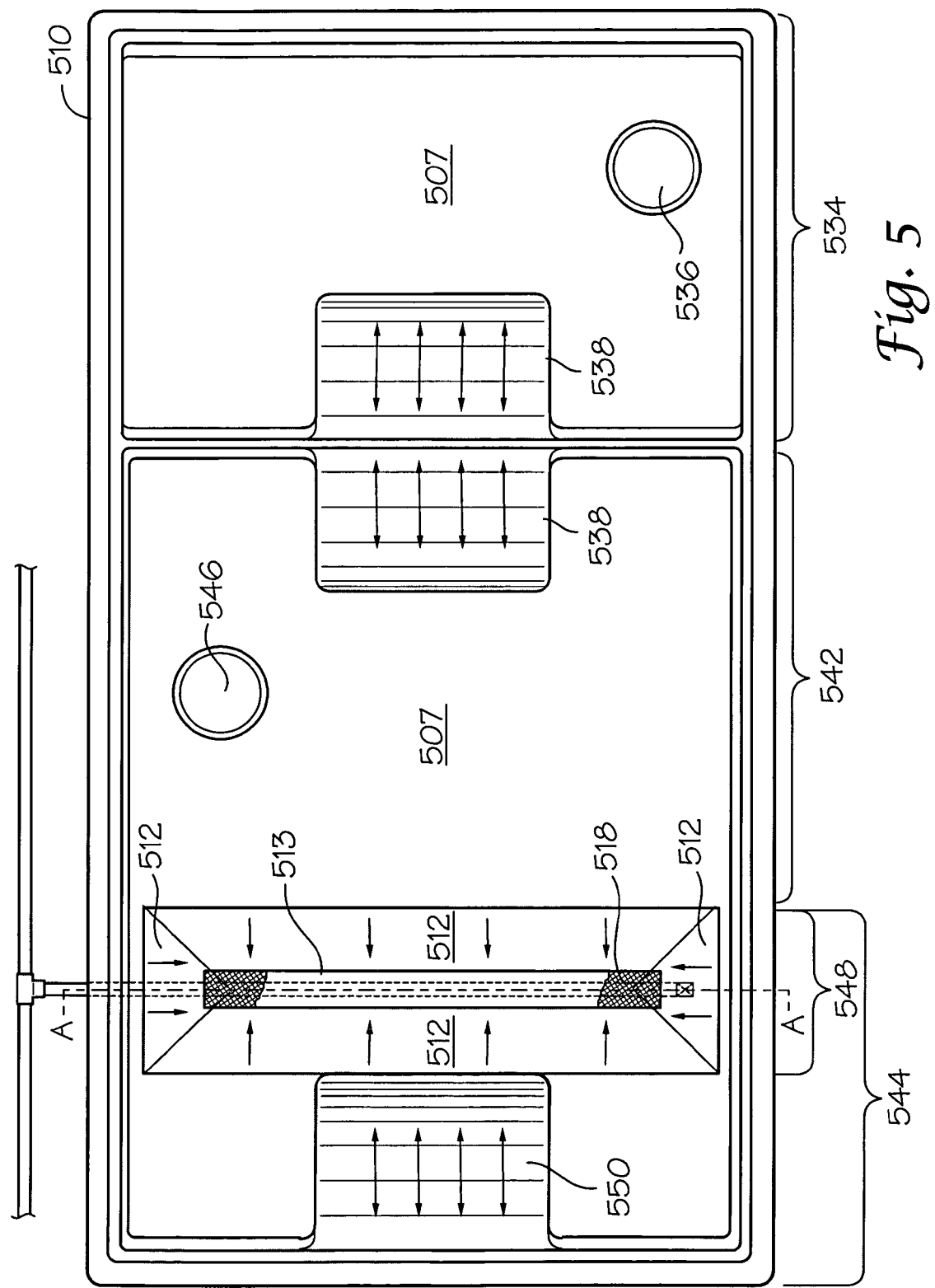
FIG. 5 is a top view of one embodiment of a growing cubicle of the present invention, comprising an air activated feed trough.

FIG. 5 is a top view of one embodiment of a frog cultivation container 510 of the present invention which shows details of floor 507. A wet area 534 typically has a water pool (or other body of water) (not shown) into which frogs go when they desire to be immersed or wetted. A drain collar 536 disposed in the floor 507 of wet area 534 provides for draining, setting of a standpipe (such as when the wet area 534 is made into a pool by use of the stand pipe), and/or setting of overflow height during cleaning with water. In some embodiments, the floor 507 of wet area 534 is sloped toward collar 536. A ramp 538 slopes up and over a dividing line 540 between the wet area 534 and a cultivation area 542 and a feeding area 544. The dividing line 540 may impose a physical barrier, such as an elevation (over which the ramp 538 passes), to separate the wet area 534 from the cultivation area 542.

A cultivation area 542 comprises a generally uniformly flat floor 507 that slopes to a drain hole 546. Drain hole 546 receives water that drips from frogs that have come from the wet area 534, and from periodic cleaning activities. A wire mesh or other barrier (not shown) may be used to cover the drain hole 546 to keep frogs from entering it.

The feeding area 544 adjacent to cultivation area 542 is comprised of a feed trough 548 comprising sloped floors 512 that slope downward to a centrally disposed elongated opening 513 covered by a perforated cover 518 (partially removed to show opening 513). The sloped floors 512, opening 513 and perforated cover 518 are analogous to components that comprise the feed trough 11 of FIGS. 2A and 2B. However, in the embodiment of FIGS. 5 and 6 the sloped floors 512 are molded into and integral with floor 507 of container 510. Apart fron the area so occupied by feed trough 548, feeding area 544 also is comprised of two sections of floor 507 separated by a feeding area ramp 550. The feeding area ramp 550 slopes downward to an adjacent part of sloped floors 512, permitting easier access for frogs to enter and/or remain next to the feed trough 548.

Figure 6:
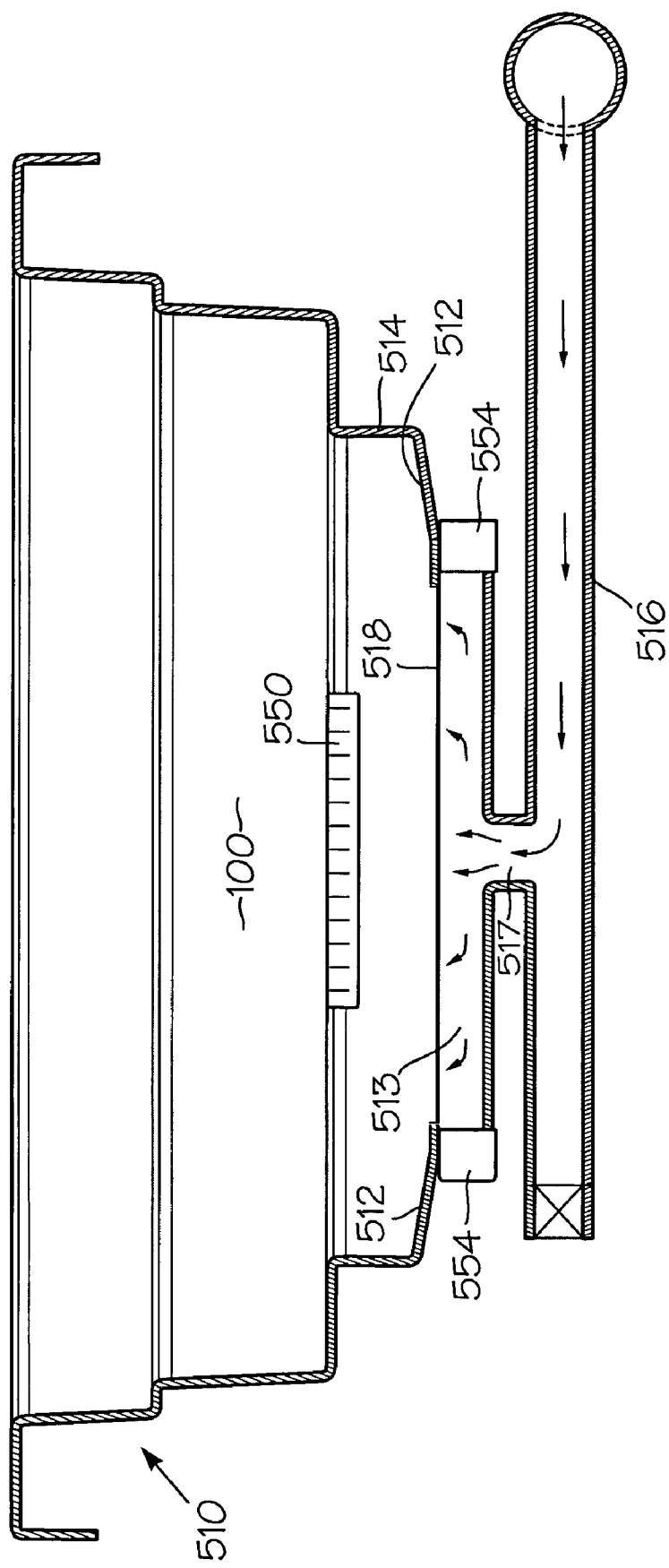
FIG. 6 is a cross-sectional view taken along axis A—A of FIG. 5, viewing toward the end of the growing cubicle having the ramp adjacent to the feed trough.

FIG. 6 provides a cross-sectional view taken along the A—A axis of FIG. 5. As observable in FIG. 6, opening 513 fluidly communicates with a space formed by pipe 552, having end caps 554, and itself in fluid communication with air inlet tube 516 via a vertical connector pipe 517. Airspace 100 also is identified in FIG. 6.

It is noted that as depicted the lower edge of the feeding area ramp 550 (i.e., nearest the sloped floors 512) is separated by a vertical distance from the nearest edge of the sloped floors 512. In other embodiments (not shown), the lower edge of the feeding area ramp 550 actually abuts with the nearest edge of the sloped floors 512. In such embodiments there is not a section of vertical wall 514 where the ramp lower edge lies.

FIG. 7 provides a cross-sectional view of another embodiment of a cultivation container 710 comprising a built-in feed trough 711. Here, built-in feed trough 711 is circular, having in certain embodiments a diameter between about 6 to about 12 inches in a cultivation container 710 that is about 30 inches across. Built-in feed trough 711 is comprised of sloped floors 712, a central opening 713, and a perforated cover 718 disposed below the central opening 713. Central opening 713 is in fluid communication with a source of forced or compressed air via a vertical connector pipe 717 fluidly communicating with an air inlet tube 716. Air inlet tube 716 in turn communicates with a larger diameter trunk line 732, which ultimately connects to the source of air, such as a compressor or blower (not shown). Airspace 100 also is identified in FIG. 7.

The embodiment depicted in FIG. 7 provides a built-in round feed trough 711 integral with cultivation container 710, which may be rectangular or square. Disposed next to the feed trough 711 is a ramp 750 sloped downward toward the feed trough 711. This permits frogs an easier access to the feed trough 711. Also, in this embodiment the perforated cover 718 is disposed a distance below the lowermost of the sloped floor 712, and below the opening 713. In view of the relative positioning of the perforated cover and the opening in this and other embodiments described herein, it is appreciated that the perforated cover may be in a relative position below, above, or even with the exact opening into the space of the feed trough. All of these relative positions are encompassed by the term "at" the opening with reference to the perforated cover.

As depicted in FIG. 5, perforated cover 718 is supported by and attached to a supportive ring 736 affixed to the inside wall of connector pipe 717. This lower positioning of perforated cover 718 provides for feed particles to drop a distance from the sloped floor, and be constrained by the side walls of connector pipe 717. This is conducive to the force of the airflow (shown by arrows) propelling upward the feed particles, rather than merely propelling feed particles to the sides, onto the sloped floors. Although the perforated cover 718 is only shown disposed in this lower position, relative to the sloped floor, in FIG. 7, it is appreciated that this positioning may be employed in any embodiment of the present invention, including those depicted in the other figures.

FIG. 7 also depicts a vibrator 760 positioned on the lower surface of the sloped floor 712. By "vibrator" is meant any mechanism for imparting vibrational forces upon an object to which it is attached, as known to those skilled in the art, and may include lower frequency, pulsation-type vibration generators. The vibrator 760 is used in certain embodiments to assist in collecting the feed from the sloped floor 712 to the perforated cover 718. For example, not to be limiting, when the airflow to propel feed into the airspace 100 of the cultivation container 710 is non-continuous, the vibrator 760 is turned on for a short period prior to one or more of the airflows so that feed that may be stuck on the sloped floor 712 is dislodged and collects onto the perforated cover 718 prior to the start of a particular airflow event. When airflow is continuous, the vibrator 760 may be turned on at specified times or at a desired frequency to assist in collecting feed particles onto the perforated cover 718, and then to be in position for being propelled into the cultivation container airspace. Although the vibrator 760 is only shown in FIG. 7, it is appreciated that a vibrator of any style and size may be employed in any embodiment of the present invention, including those depicted in the other figures.

The vibrator 760 also is used in certain embodiments as a back-up when the air supply fails and there is a need to move feed particles along the sloped floor. Vibrating with a vibrator such as 760 in such circumstance will provide for a period of movement of feed particles along a sloped trough floor, during which time the captive amphibians may be stimulated to feed.

More generally, a vibrator also may be the sole means for moving feed particles in a feed collection area to simulate live feed movement to stimulate feeding in the amphibians in the cultivation container. The vibrator may operate to continue to move feed particles even as food particles collect in one or more areas of the floor that are low relative to other areas. Alternatively, a vibrator maybe used in combination with any device that is able to propel or otherwise redistribute feed particles to a higher part of the floor of the feed collection area. Thus, a means for moving feed particles in a feed collection area may include, but is not limited to, propelling feed particles using an airflow through a perforated cover (with or without vibrating feed particles that are on the floor of the feed collection area), and vibrating feed particles that are on the floor of the feed collection area. Accordingly, air, vibrational, or other force known to those skilled in the part, or later developed, is provided to move the feed particles within the container, particularly in the feed collection area, to simulate live feed and thereby stimulate feeding behavior and achieve feeding.

Figure 8A:
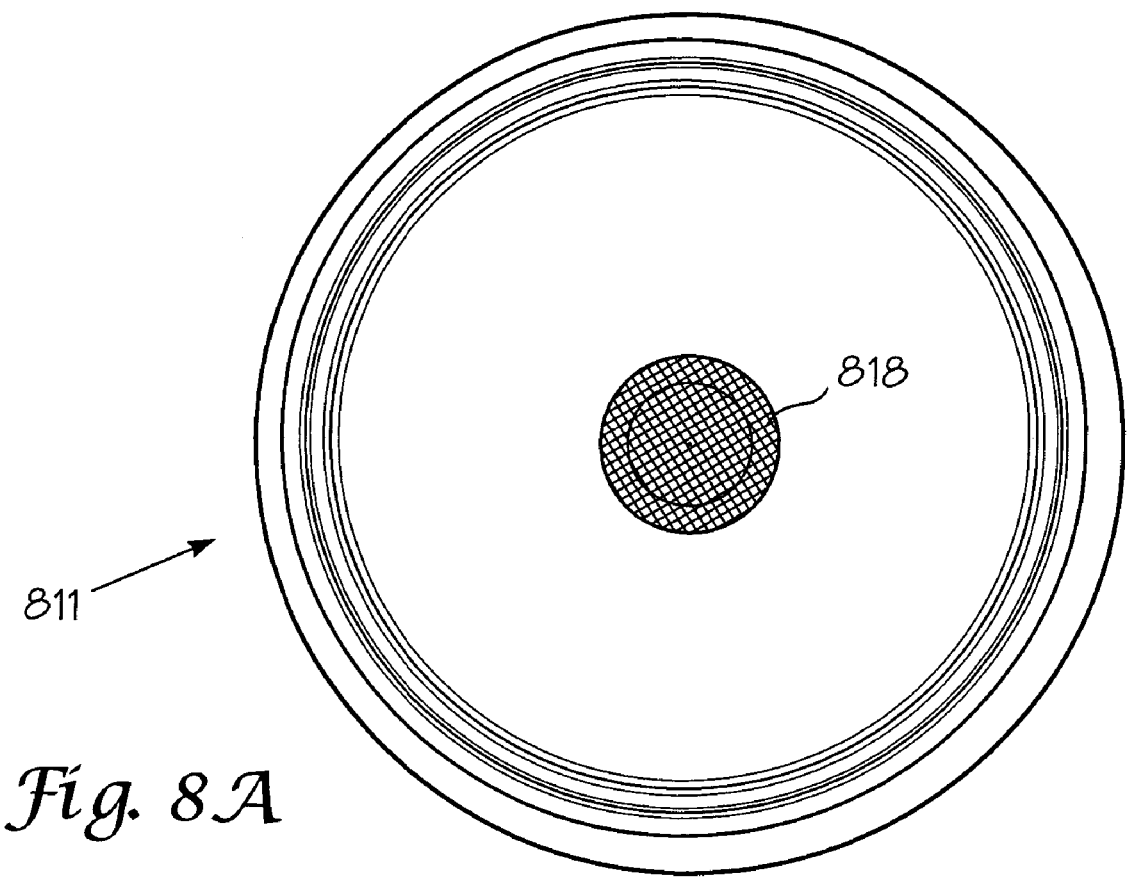
FIGS. 8A and 8B provide, respectively, a top and a cross-sectional view, through the middle, of one embodiment of a circular air-activated feed trough which, among other features, has a steeper floor angle than the embodiment depicted in FIGS. 2A and 2B.
Figure 8B:
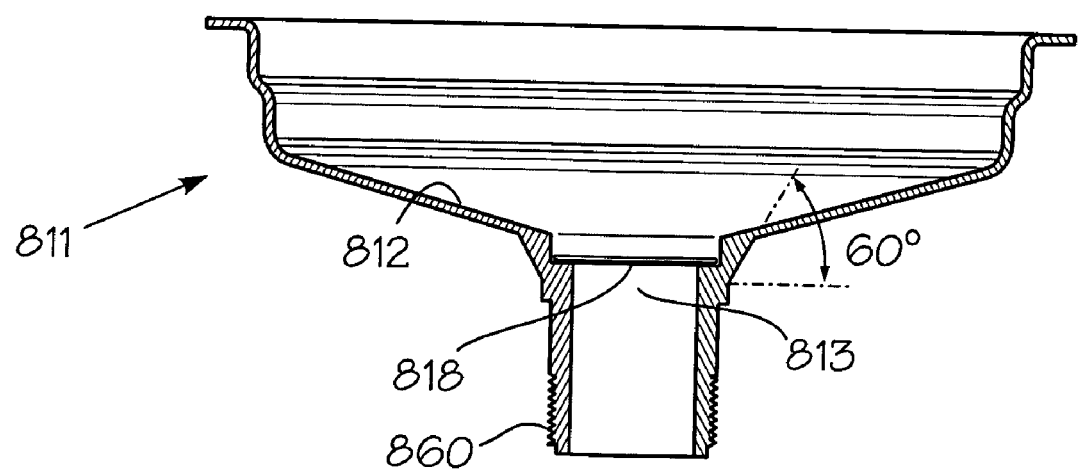

FIGS. 8A and 8B depict top and side cutaway views, respectively, of a circular feed trough 811 that may be fabricated, as by injection molding, separately from a cultivation container, such as a growing cubicle, and then installed into such cultivation container. Standard PVC pipe threads 860 are provided to allow for rapid connection to a piping system having a matching female thread. In this embodiment, a steeper angle of the sloped floor 812 is provided, namely, about 25 degrees.

Further as to the perforated cover of the feeding trough, it is appreciated that under certain circumstances moist feed particles may fall onto it and become stuck to it. Thus, in certain embodiments a vibrator or impact device may communicate with the perforated cover, and may periodically be activated to vibrate or strike the perforated cover so as to dislodge such stuck-on feed particles. For instance, not to be limiting, a solenoid-activated rod may be directed to the frame of the perforated cover, and the perforated cover may be mounted on a rubberized mounting so as to be movable within a range, and upon activation the solenoid pushes the rod which sharply jars the perforated cover, thereby dislodging the stuck-on feed particles. This is one example, not to be limiting, of a pulsation-type vibration generator.

Vibration or impact such as this, directed to the perforated cover, or the normal breaking apart of feed particles, may result in fine particles of feed falling through the perforated cover and into the air lines (such as 16, 516, 716, etc.). However, the majority of the mass of the feed particles is retained on the perforated cover and is propelled into the cultivation container airspace until consumed. As indicated, in one example, not to be limiting, a valve at the end of the air lines provides for periodic clean-out of the air lines, which removes such fine particles. In another example, not to be limiting, each cultivation container has its own valve to control the rate of airflow (and this valve may be inline with the air supply, thereby restricting flow, or an exhaust valve, releasing excess air (as exemplified by the rigid tee example above).

As disclosed herein, air flows into the cultivation containers via an opening in the feed trough at a sufficient force to resuspend feed particles for a period. It is noted that in some embodiments the air being flowed into the cultivation containers is heated to elevate its temperature. Any heating device known in the art, or later developed, suitable for heating the air, may be employed. The heating of the air functions in one or more of the following ways:

1. Dries feed particles that have become moist or wet. This reduces or prevents feed spoilage. Also, a drier feed particle weighs less than a wet one and accordingly becomes airborne more easily.
2. Dries areas of the floor of the cultivation container that have become wet. This is desirable in certain situations and for certain reasons, such as to reduce the wetting of feed particles as frogs pass into the feed trough area. With a drier floor near the feed trough, there is less likelihood of the frogs wetting feed particles.
3. Raises the temperature inside the cultivation container. This increases the metabolism of the frogs, and, when properly controlled, provides for increased growth rates. For instance, not to be limiting, the airflow is heated to maintain an ambient temperature in the cultivation containers within the range of 40 to 85 degrees Fahrenheit.

The elevation of the air temperature is dictated by a number of factors, some of which are countervailing and must be balanced for a particular set of factors. For instance, in the summer when the ambient temperature is relatively high, even though drying with warmer air is desirable to dry the feed, the elevation of air temperature may be limited by a desire to not exceed a certain cultivation temperature limit so as to not stress the frogs. During cooler ambient temperatures in the winter, in contrast, this limitation is not as great, and greater heating of the air can lead to a desirable increase in container temperature and increased growth rates (along with effective drying of pellets). Humidity also may be controlled.

It is appreciated that various substitutions for specific structures and arrangements may be made while keeping within the scope of the present invention. As but one example, instead of the perforated cover being comprised of a wire mesh or screen, a perforated cover may be comprised of a plate having a plurality of holes or slits, with the air passing through such holes or slits, so long as the functional requirements of the perforated cover are met (i.e., retain the feed particles and have sufficient open area to provide airflow sufficient to propel the feed particles into the airspace of the cultivation container).

More generally, while the preferred embodiments of the present invention have been shown and described herein in the present context, such embodiments are provided by way of example only, and not of limitation. Numerous variations, changes and substitutions will occur to those of skilled in the art without departing from the invention herein. For example, the present invention need not be limited to best mode disclosed herein, since other applications can equally benefit from the teachings of the present invention. Accordingly, it is intended that the invention be limited only by the spirit and scope of the appended claims.

What is claimed is:

1. A system for cultivating amphibious animals, comprising:

at least one container having a floor supporting the animals, and sidewalls connected to the floor extending upward there from and forming an interior of the container;

a feed collection area formed in the container floor supporting feed for animals; and, a means, operatively connected to the container, for moving the feed particles within the feed collection area to simulate live feed.

2. The system of claim 1, the means for moving comprising discharging air through an air opening disposed in the feed collection area to move the feed particles on a perforated cover at the opening, the air from an air supply source is operatively connected to the container through the air opening in the feed collection area.

3. The system of claim 2 wherein the feed collection area comprises a trough depending from a floor of the container, comprising at least one trough floor inclined downward to the air opening, and having a top opening in communication with the interior of the container, and said container is supported in spaced relation to a floor of a cultivating room.

4. The system of claim 3 comprising an air blower as the air supply source.

5. The system of claim 4, the feed dispenser comprising a feed container for receiving and storing feed particles, the feed container having at least one opening at its bottom, a plate disposed across the bottom, spaced a distance from the bottom to permit feed particles to pass, and a rod pivoting from the container, attaching to the plate, and extending into the container, adjusted to tilt the plate to distribute feed particles upon a movement of the rod.

6. The system of claim 4 additionally comprising a heater to heat the air so as to maintain a temperature between about 40 and about 85 degrees Fahrenheit in the container.

7. The system of claim 1 additionally comprising a feed dispenser disposed above the feed collection area of the at least one container.

8. The system of claim 1, the means for moving comprising a mechanism for vibrating the feed collection area.

9. A system for feeding amphibious animals, comprising:

an upright rack;

a plurality of containers, within which the amphibious animals are cultivated, supported on the rack and each container having a floor and sidewalls connected to the floor extending upward there from and forming an interior of the container;

an artificial feed source in communication with each container for dispensing artificial feed into each container;

a trough depending from the bottom of the container, having a top opening in fluid communication with the interior of the container and supporting feed for animals; and, an air supply source in fluid communication with the trough on each container and discharging air through the trough to move the feed in the trough.

10. A method for feeding frogs cultivated in captivity, comprising the steps of:

providing at least one cultivation container in which the frogs are cultivated, said container having a feed collection area on and extending below a floor of the at least one cultivation container;

dispensing artificial feed within the container to the feed collection area; and, providing a force to the container to move the artificial feed within the container to simulate live feed.

11. The method of claim 10, the providing a force comprising discharging air through an air opening in the feed collection area to move the feed, the air from an air supply source in fluid communication with the container through the feed collection area.

12. The method of claim 10, the providing a force comprising vibrating the feed collection area.

13. An air-activated feed trough assembly for use in a cultivation container for culture of amphibians, comprising:

a. a trough body comprising an outer perimeter adapted to join a floor of the cultivation chamber, comprising a trough floor sloping downward front said outer perimeter to an air opening;

b. perforated cover at the air opening, forming a surface on which to collect feed particles;

c. an air supply line connecting to said air opening; and d. a source of air in fluid communication with the air supply line.

14. The air-activated feed trough of claim 13 additionally comprising a vertical wall disposed between the outer perimeter and the trough floor.

15. A method to present feed particles to amphibians in a cultivation container comprising:

a. in a feed collection area of the cultivation container, comprising at least one sloped floor sloping downward to an opening in fluid communication with a source of air, collecting feed particles from the at least one sloped floor on a perforated cover disposed at the opening; and b. propelling feed particles from the perforated cover into the airspace with an airflow through the opening from the source of air.

16. The method of claim 15, said collecting comprising passive rolling of feed particles from points on the at least one sloped floor, the points being landing points from landing of feed particles after a period of said propelling.

17. The method of claim 16, said collecting additionally comprising activating a vibrator affixed to the feed collection area, wherein said vibrating moves feed particles that had become stationary on the at least one sloped floor.

* * * * *